United States Patent
Hang (10) Patent No.: US 8,435,031 B2
(45) Date of Patent: May 7, 2013

(54) ORTHODONTIC CLASP

(76) Inventor: William M. Hang, Westlake Village, CA (US)

( * ) Notice: Subject to any disclaimer, the term of this patent is extended or adjusted under 35 U.S.C. 154(b) by 244 days.

(21) Appl. No.: 12/783,814

(22) Filed: May 20, 2010

(65) Prior Publication Data

US 2011/0287377 A1 Nov. 24, 2011

(51) Int. Cl.
  *A61C 3/00* (2006.01)
(52) U.S. Cl.
  USPC .................................. 433/7; 433/6
(58) Field of Classification Search ........... 433/6, 7; 29/896.1, 896.11
  See application file for complete search history.

(56) References Cited

U.S. PATENT DOCUMENTS

| | | | |
|---|---|---|---|
| 3,434,210 A | 3/1969 | Sage | |
| 3,454,001 A | 7/1969 | Stockfisch | |
| 4,026,023 A * | 5/1977 | Fisher | 433/7 |
| 4,054,996 A | 10/1977 | Wallshein | |
| 4,468,196 A | 8/1984 | Keller | |
| 4,573,914 A | 3/1986 | Nord | |
| 5,002,485 A * | 3/1991 | Aagesen | 433/7 |
| 5,087,196 A | 2/1992 | Polanco | |
| 5,096,416 A * | 3/1992 | Hulsink | 433/6 |
| 5,131,843 A | 7/1992 | Hilgers et al. | |
| 5,145,364 A * | 9/1992 | Martz et al. | 433/6 |
| 5,368,477 A | 11/1994 | Neeley | |
| 5,580,243 A * | 12/1996 | Bloore | 433/6 |
| 5,607,300 A * | 3/1997 | Tepper | 433/6 |
| 5,829,970 A | 11/1998 | Yousefian | |
| 6,213,766 B1 | 4/2001 | Di Massa | |
| 6,435,871 B1 * | 8/2002 | Inman | 433/7 |
| 7,780,445 B2 * | 8/2010 | Keles | 433/24 |
| 2007/0059659 A1 * | 3/2007 | Da Cruz | 433/6 |
| 2008/0057457 A1 * | 3/2008 | Inman | 433/6 |
| 2008/0220388 A1 * | 9/2008 | Weissbach Otte | 433/7 |
| 2009/0087810 A1 * | 4/2009 | Singh | 433/24 |

* cited by examiner

*Primary Examiner* — Todd Manahan
*Assistant Examiner* — Matthew Nelson
(74) *Attorney, Agent, or Firm* — Sanford Astor; Brooks Kushman P.C.

(57) ABSTRACT

A new and useful orthodontic clasp that is more resistant to breakage, and when in use is unlikely to separate from its associated orthodontic appliance should breakage occur, comprising two metal wires crossed at an angle and held together with a weld/solder joint, said weld/solder joint having four wire segments extending from said two metal wires crossed at the weld/solder joint, two of said wire segments adjacent and longer in length and two of said wire segments adjacent and shorter in length, said four wire segments each having a clasp wire bend.

13 Claims, 6 Drawing Sheets

ORTHODONTIC CLASP

FIELD OF THE INVENTION

This invention relates to a new and useful orthodontic clasp designed for both orthodontic utility and for increased strength and resistance to breakage.

BACKGROUND OF THE INVENTION

Heretofore, orthodontic clasps have had a number of associated problems. These problems include, but are not limited to, a design that is uncomfortable for the patient and not easily adjusted for orthodontic treatment, a design that is not structurally sound and resistant to breakage, and a design that does not secure the clasp to the orthodontic appliance should breakage occur.

During the course of orthodontic treatment, adjustments to the orthodontic appliance are routinely made for treatment to progress. A commonly used clasp is known at the Crozat Clasp, which has a significant chance of breakage when adjustments are made using pliers, the instrument of choice for making such adjustments.

Another clasp, known as the Adams Clasp, is commonly used in removable orthodontic appliances, but has poor retention, and is difficult to adjust for better retention.

BRIEF SUMMARY OF THE INVENTION

Applicant's invention comprises an orthodontic clasp which is relatively comfortable for the patient, easy to adjust for optimal retention; and is much more structurally sound than orthodontic clasps presently in use. This new clasp provides an orthodontic appliance, on which it is used, with superior retentive strength. For instance, the Crozat Clasp provides no retention at all if its solder joint breaks, since the clasping part falls off entirely. The orthodontic appliance using the Crozat Clasp will then fall out of the patient's mouth.

The orthodontic clasp of this invention continues to provide retention if its weld/solder joint breaks, since the retaining part of the orthodontic clasp, comprising two clasp anchors, still remain embedded in the acrylic portion of the orthodontic appliance, in which it is used. Thus, if the orthodontic clasp breaks, no time is lost in treatment, since the orthodontic appliance can still be worn, and will often still function to provide retention of the appliance until any needed repair or replacement is made. Commonly used clasps today do not have this advantage, and there may be considerable time lost in treatment.

When in use, the orthodontic clasp is attached to its associated orthodontic appliance through two clasp anchors that are anchored in the acrylic portion of the orthodontic appliance.

This orthodontic clasp invention is also intended to include a pre-assembled or partially assembled version of the orthodontic clasp, when it is incorporated into a kit and the like, that may be used in assembling or manufacturing an orthodontic appliance that may use one or more of the orthodontic clasps.

The term "orthodontic appliance", as used throughout this specification and its appended claims, is intended to refer to a broad range of orthodontic appliances, and particularly including, but not limited to, those with a portion comprised of acrylic, or the like, where clasp anchors of the orthodontic clasp are embedded into the acrylic.

An associated new and useful orthodontic appliance, called the "Hang Expancer", described in the inventor's co-pending U.S. patent application Ser. No. 12/731,649, incorporated herein by reference in its entirety, is an example of such an orthodontic appliance where the orthodontic clasp has a new and useful application. The Hang Expancer is so named because it is traditional for new embodiments of medical devices, such as this new and useful type of orthodontic appliance, to be named after its inventor, in this case, the present inventor, Dr. William M. Hang, to distinguish it from other orthodontic appliances.

The term "Expancer" is derived from the fact that the aforementioned orthodontic appliance both expands the maxillary palate and advances the upper front teeth, hence the name Expancer. The new and useful Hang Expancer is shown in FIGS. 5-8, with an orthodontic clasp located on each side of this embodiment of an orthodontic appliance.

The term "acrylic" as used throughout this specification and its appended claims is intended to be broadly construed to include, essentially, a wide range of related polymeric materials, some of which may not be chemically classified as an acrylic, but as a functionally equivalent chemical. The term "acrylic" is also intended to include chemical mixtures composed essentially of acrylic, but also optionally including other chemicals or substances, such as colorants or dyes for adding a desired tint or color to the acrylic, such as a blue or a light red color. The term "acrylic" is used herein as the material of choice for acrylic used in orthodontic appliances that may use the orthodontic clasp of this invention, but the term may also include other functionally equivalent polymeric materials. The acrylic formulation used in the manufacture of the orthodontic appliances cited throughout this specification, and its appended claims, typically use a cold-cured or salt-and-pepper method of forming the acrylic element of the orthodontic appliance.

The term "metal" as used throughout this specification and its appended claims is intended to be broadly construed to include a broad range of metallic elements and alloys. The two metal wires joined together at a weld/solder joint to form the orthodontic clasp of this invention are preferred to be composed essentially of stainless steel wire. The metal wire is also preferred to be heat-treated for stress relief after the orthodontic clasp is bent and formed to fit the appliance.

The term "anchor" as used throughout this specification and its appended claims is intended to be broadly construed and is intended to refer to the portion of the two wires on the orthodontic clasp that are embedded in the acrylic portion of an orthodontic appliance, such as a Hang Expancer.

The term "crimp" or "crimped" as used throughout this specification and its appended claims is intended to be broadly construed, and is intended to refer to portions of the clasp anchors of the orthodontic clasp that are embedded in acrylic.

The present invention is a new and useful orthodontic clasp which is a significant advance in the art. This orthodontic clasp, when in use, is anchored to an associated orthodontic appliance and has a clasp weld/solder joint. Should this clasp weld/solder joint fail or break, the orthodontic clasp will maintain its general form and functionality for a matter of days or longer, until said break is repaired, or the orthodontic appliance may be replaced by an orthodontist. This orthodontic clasp is less prone to failure and breakage, easier to adjust by the orthodontist, and is more effective in treating patients if breakage should occur, as there would be little or no interruption in treatment due to the anchoring of the orthodontic clasp in the acrylic portion of its associated orthodontic appliance.

The orthodontic clasp is comprised essentially of two wires crossed at an angle with a weld/solder joint, thereby causing four wire segments and their four wire ends to extend from the weld/solder joint. The two wires are held together at adjacent angles that are typically of about 45° and 135°, as shown in FIGS. 1-4, with a weld and a silver solder joint. The four wire segments extending from the weld/solder joint are the two clasp anchors, the mesial wire, and the distal wire.

Once the two wires are attached with a weld/solder joint, the four wire segments extending from the weld/solder joint are each bent with a clasp wire bend, so that the orthodontic clasp will fit around a patient's tooth, usually a molar. When in use, this orthodontic clasp is held in place in the acrylic portion of an associated orthodontic appliance, by embedding the two clasp anchors into the acrylic, as shown, for example, in FIGS. 5-8. The two wires extending from the weld/solder joint that are not embedded into the acrylic are the mesial clasp and the distal clasp, which engage the tooth, as shown in FIGS. 5-8. The aforementioned angles where the two wires are attached with a weld/solder joint, may vary significantly, according to the patient's needs, and may be, for example, approximately 20° and 160° to approximately 60° and 120°, as needed.

Two of the four wire bends on an orthodontic clasp form a clasp anchor and these anchors are embedded into the acrylic, as shown in FIGS. 5-8, when the orthodontic clasp is in use. The clasp anchors are preferred to be crimped. The clasp anchors when embedded in the acrylic also serve to reinforce the structural strength of the acrylic, and to prevent the acrylic from breaking, much as rebar is used to reinforce concrete.

BRIEF DESCRIPTION OF THE DRAWINGS

The objects, features and advantages of the invention will be apparent from the following description of the embodiments of the invention, as illustrated in the accompanying drawing figures, in which like reference numerals refer to the same parts or elements of the invention, throughout the different views and the specification. The drawing figures are not necessarily drawn to scale, as emphasis is instead being placed upon illustrating the principles of the invention.

DETAILED DESCRIPTION OF THE INVENTION

There may be some variation in the embodiments of the orthodontic clasp, depending on the patient and the orthodontic appliance used to meet the patient's needs. Most orthodontic appliances will use two orthodontic clasps, but some appliances may use more than two. The preferred embodiment of the orthodontic clasp is that suited for most patients and for most applications of the invention. Some patients have special areas that may require some variation in the orthodontic clasp shape.

Figure 1:
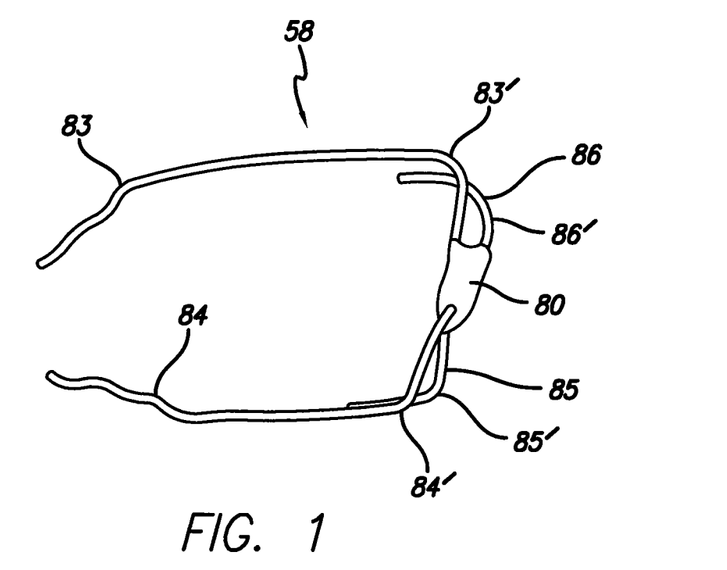
FIG. 1 is a top plan view of the orthodontic clasp.
Figure 2:
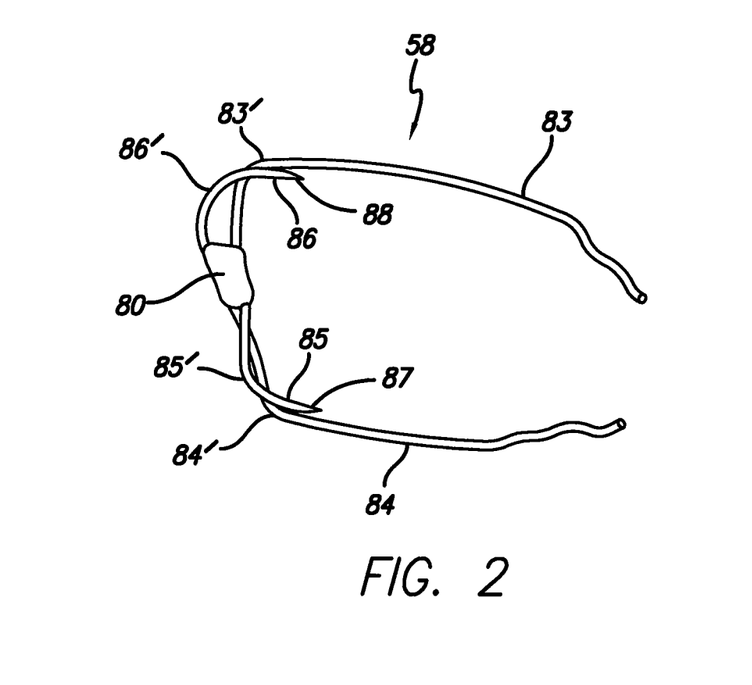
FIG. 2 is a bottom plan view of the orthodontic clasp.
Figure 3:
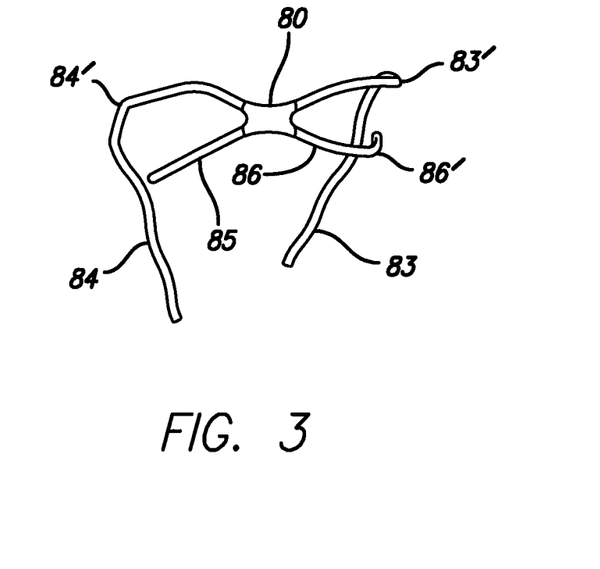
FIG. 3 is a perspective view of the orthodontic clasp.
Figure 4:
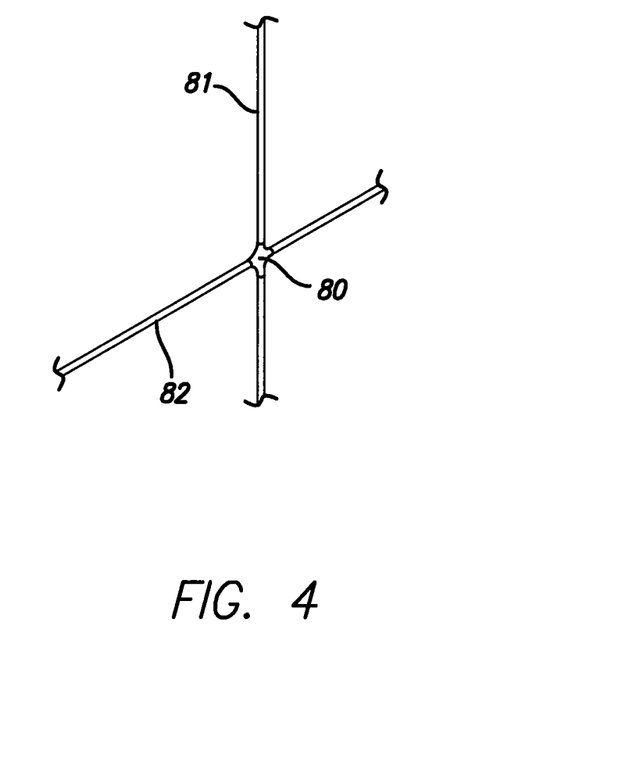
FIG. 4 is a top plan view of the orthodontic clasp wires before they are bent into shape.
Figure 5:
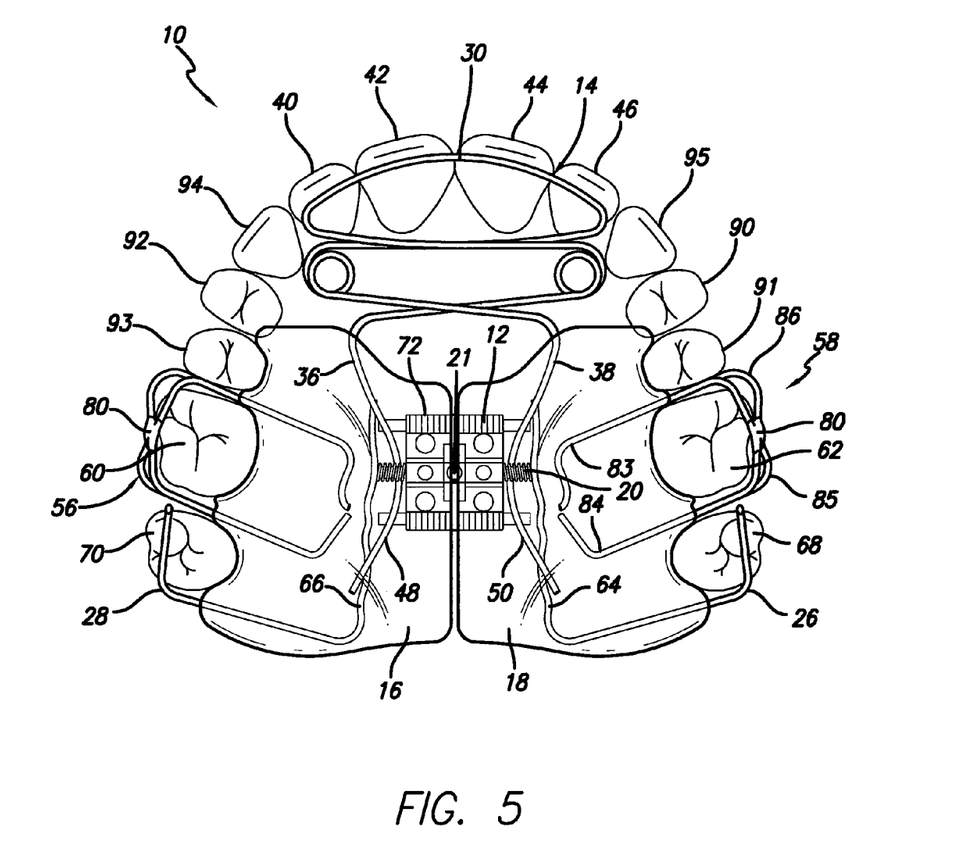
FIG. 5 is a bottom plan view of an orthodontic appliance utilizing the orthodontic clasp.
Figure 6:
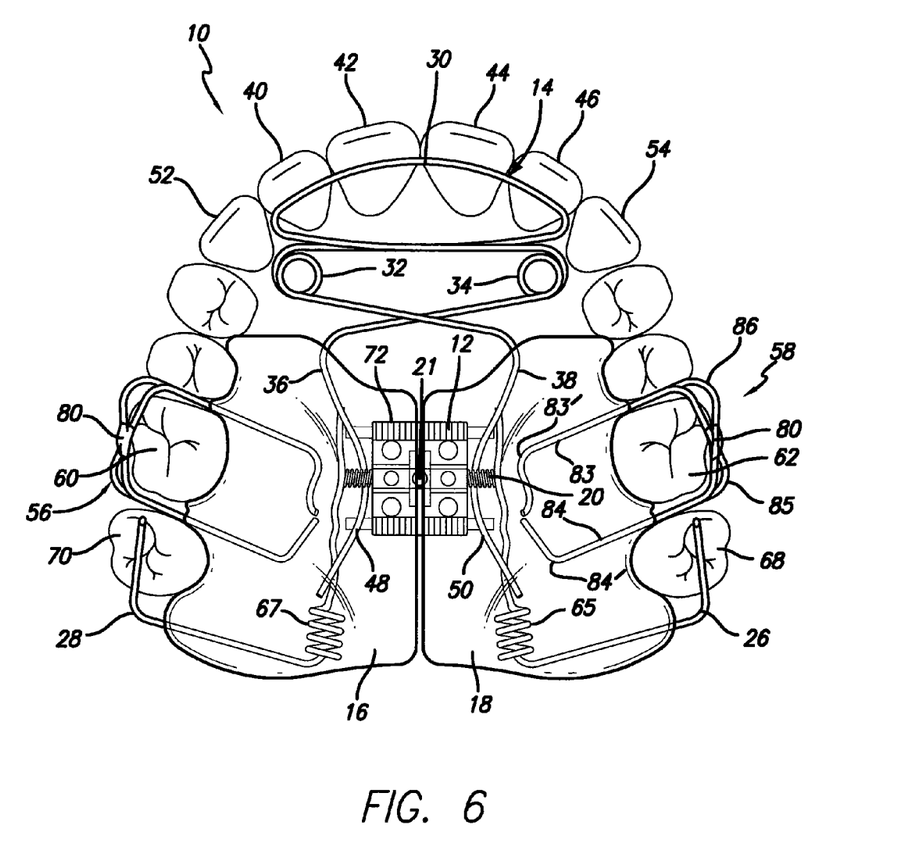
FIG. 6 is a bottom plan view of another embodiment of an orthodontic appliance utilizing the orthodontic clasp.
Figure 7:
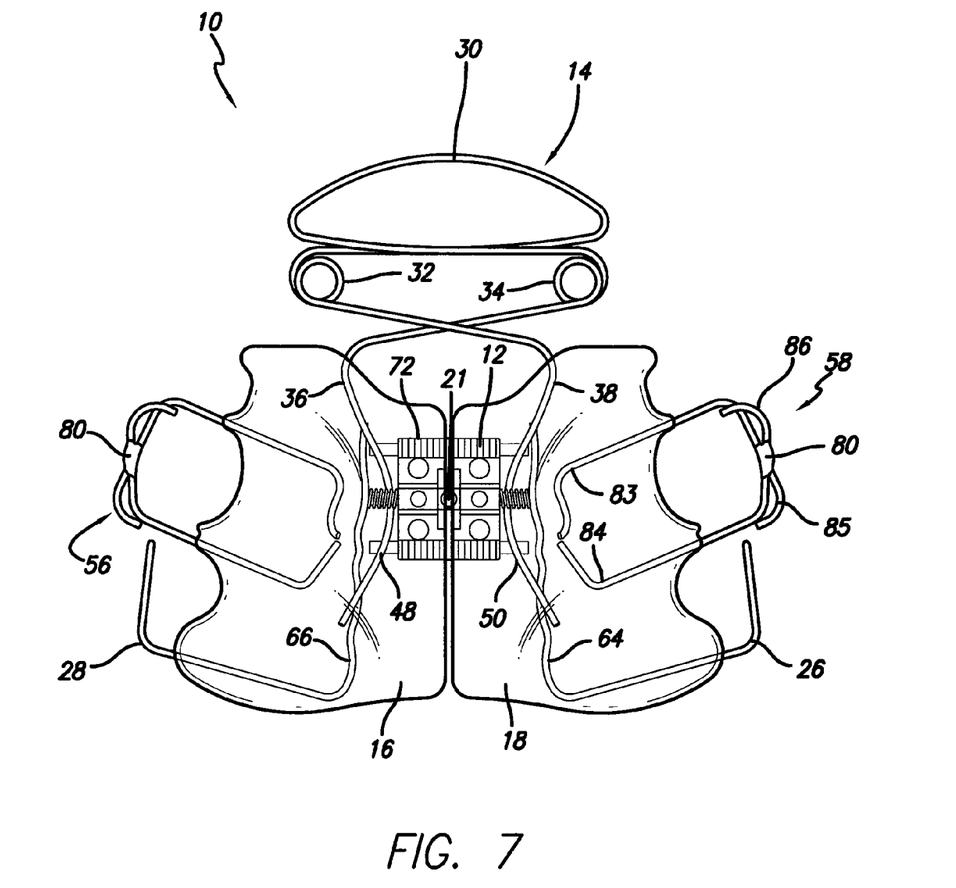
FIG. 7 is a bottom plan view of the embodiment of FIG. 5, with the depiction of the teeth removed.
Figure 8:
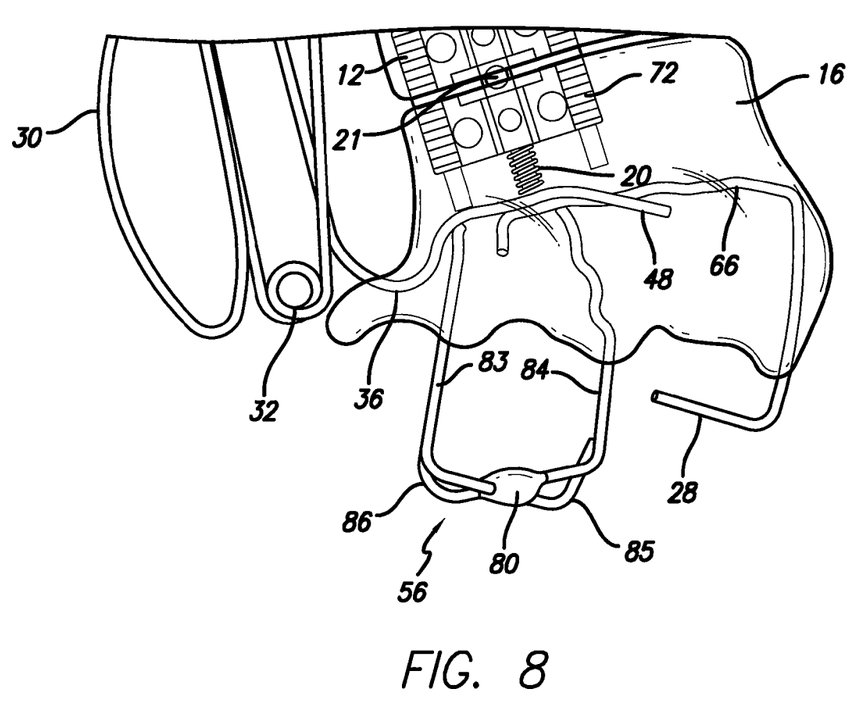
FIG. 8 is a perspective left side view of the embodiment of FIG. 7.

Referring to FIGS. 1-4, a simple embodiment of the orthodontic clasp is comprised essentially of only the bare essential elements for the simplest embodiment of the invention. A simple embodiment of the orthodontic clasp (58) is comprised essentially of two wires (81, 82) attached at a joint (80) with a weld/solder joint (FIG. 4). The two wires (81, 82) are usually attached at a set of angles of between 20° and 160° and about 60° and 120°, depending upon the needs of the patient. The two attached wires (81, 82) and their four associated wire segments (83, 84, 85, 86) and wire ends extending from the weld joint may be formed into a clasp by bending each of the four wire segments (83, 84, 85, 86) to a rounded angle of approximately 90 degrees, essentially as shown in FIGS. 1-3, to form a clasp wire bend, to fit along a patient's molar (60, 62), as desired, and as shown in FIG. 5. Two (85, 86) of these four wire ends are trimmed to fit along the embrasures of molar (62), as shown in FIG. 5, and are termed the mesial wire (86) and the distal wire (85). The remaining two wire segments (83, 84) extending from the clasp weld/solder joint (80) and their respective clasp wire bend are each longer than the mesial wire (86) and the distal wire (85), and are each termed the clasp anchors (83, 84) and are embedded at their end portions in the cold-cured acrylic portion of an orthodontic appliance, when the orthodontic clasp is in use.

When the orthodontic clasp is prepared for a patient, its precise shape and size and its position in an orthodontic appliance, such as a Hang Expancer, is adjusted by the orthodontist, using pliers or the like, to precisely fit the patient. Therefore, there may be some variance in the relative size, shape, and position of the orthodontic clasp.

Modified simple embodiments of the orthodontic clasp are comprised essentially of the elements of the simple embodiment of the orthodontic clasp, with one or more additional elements added to enhance the embodiment. Such additional elements to enhance the orthodontic clasp include anyone or more of the following elements, as indicated below.

The two clasp anchors (83, 84) may each have an anchor wire bend 83' 84' so that when the orthodontic clasp is in use, the clasp anchors (83, 84) would optimally be directed toward and anchored in the cold cured acrylic (16, 18) body of an orthodontic appliance, as shown in FIGS. 5-8.

The two clasp anchors (83, 84) may each have one or more crimps (87, 88) in one or more planes, in the portion of the clasp anchors (83, 84) that would be embedded in the acrylic (16, 18), when in use in an orthodontic appliance, as shown in FIGS. 5-8. The crimps (87, 88) add stability to the positioning of the orthodontic clasps (56, 58), making them more securely affixed to the acrylic (16, 18) portion of an orthodontic appliance, when in use.

The ends (87, 88) of mesial wire (86) and distal wire (85) as shown in FIG. 2, may be ground and sharpened, using a power green stone grinder or the like, to more easily fit the mesial wire (86) and distal wire (85) into the two embrasures of the primary teeth involved.

Mesial wire (86) and distal wire (85) are each much shorter in length than clasp anchors (83, 84) because clasp anchors (83, 84) must extend into acrylic region (16, 18) when in use in an orthodontic appliance. The shorter mesial wire 86 and distal wire (85) are not embedded in acrylic (16, 18) when the orthodontic clasp is in use, but are to be adjusted to fit snugly against a patient's primary upper or lower molar, permanent molar, or permanent bicuspid tooth, thereby positioning the orthodontic clasp and its associated orthodontic appliance snugly onto the patient's palate, teeth and related soft tissue, as shown in FIGS. 5-8.

A Preferred Embodiment Utilizing the Orthodontic Clasp

Referring now to FIGS. 5-8, there is shown the use of the orthodontic clasp of this invention on an orthodontic appliance known as the Hang Expander, referred to above.

The orthodontic appliance (10) known as the "Hang Expander" functions as both an expander of the maxillary arch and an advancer of the upper front teeth. The appliance (10) comprises an expansion assembly (12) and an advancer (14) embedded into each of two acrylic palatal halves (16, 18) of the appliance, thereby holding the two halves firmly together as a single appliance contoured to the patient's hard palate. Expansion assembly (12) comprises a screw (20) which is turned to adjust the lateral movement of the two palatal halves (16, 18).

Appliance (10) further comprises two orthodontic clasps (56, 58) and two molar intrusion wires (26, 28) one of each embedded into each side of the two acrylic palatal halves (16, 18).

The advancer (14) comprises a single wire wound into an advancing wire section (30), two advancing wire helix sections (32, 34), and two advancing wire anchor sections (36, 38).

The two advancing wire anchor sections (36, 38) are each embedded in and anchored to the separate acrylic halves (16, 18) and protrude from the front of each acrylic half (16, 18) then forming the two helix sections (32, 34) and the advancing wire section (30) which protrudes from the front of the appliance, in a generally half-oval shape, adapted to press against the back of the four incisors (40, 42, 44, and 46).

The two wire helices (32, 34) are located between the rear of the advancer wire (30) and the front of the wire anchors (36, 38). The helices (32, 34) provide a gentle force to the advancing wire section (30) on the upper front teeth (40, 42, 44, and 46). The upper front teeth, the incisors, (40, 42, 44, and 46) sometimes along with the two cuspids (52, 54) may be bonded together with braces (not shown), so that they are all pushed forward together by advancer (30).

Each of the two advancing wire anchors (36, 38) may have crimps (48, 50) or the like, near their terminal ends, to stabilize their set in their respective acrylic half (16, 18) effectively preventing the advancer (30) from coming loose or sliding out of one or both of the acrylic halves (16, 18).

Each of the two outer sides of the acrylic halves (16, 18) along their mid-regions, has an orthodontic clasp (56, 58) embedded therein. Clasps (56, 58) fit around a molar tooth, generally the primary second molar (60, 62) to help hold the entire appliance (10) in place.

Near the rear region of the side of each of the two acrylic halves (16, 18), there is a molar intrusion wire (26, 28). Each of the two molar intrusion wires (26, 28) has an anchor portion (64, 66) or (65, 67 of FIG. 6) which is embedded and anchored to the rear portion of a separate acrylic half (16, 18). The anchor portion (64, 66) of the molar intrusion wire (26, 28) that is embedded in the acrylic half (16, 18) may be crimped to stabilize and secure its position. The molar intrusion wire (26, 28) sits on the top of a molar tooth (68, 70) and presses on the molar (68, 70) to intrude them into the gums of the patient, if such treatment is needed. If such treatment is not needed, intrusion wires (26, 28) are not present as a part of the orthodontic appliance.

The wire comprising the advancer (30) the orthodontic clasps (56, 58) and the molar intrusion wires (26, 28), and their associated elements and anchors, may be a heat-treated stainless steel wire with a gauge thickness of approximately 0.032 inch. The wire composition, and particularly its gauge thickness, may vary according to the needs of the patient and judgment of the orthodontist. The wire gauge thickness may range from about 0.030 to about 0.036 inches, preferably about 0.032 inches.

An alternative to stainless steel wire is TMA wire (Titanium Molybdenum Alloy wire) with wire gauge thickness of about 0.030 to about 0.038 inches, preferably about 0.036 inches in diameter. TMA wire, which is available from Great Lakes Orthodontics, of Tonawanda, N.Y., is comprised essentially of Ti: 70-80%, Zr: 5-10%, Sn: 4-8%, and Mo: 10-20%. TMA wire provides a very light force for a given activation of advancement. It is much lighter than stainless steel for an equal amount of activation. TMA wire can make a larger activation which will result in a larger movement of the teeth with less discomfort to the patient. A less frequent appointment interval in which the patient needs to return to the office for additional activation is also an advantage. With one activation the teeth will move farther than with stainless steel.

Applicant has discovered that the TMA wire provides a lighter force on the teeth, which actually will move the teeth faster with less discomfort. The teeth move faster because less pressure is placed on the root/bone interface. Less pressure means less disruption to the blood supply of the tooth. More blood supply to the tooth means that the process of bone resorption, which makes the space into which the tooth will move, will occur faster. Greater forces essentially disturb the blood supply more and a new blood supply must be made through the bone to have the resorption process (osteoclastic activity) occur. Because the body must make a new blood supply to the area, there is a lag in tooth movement with heavier forces. There is a very big advantage to the patient including less discomfort and faster tooth movement with lighter forces.

The orthodontic appliance is typically composed essentially of acrylic, as noted above, and is formulated by combining a polymeric powder with a monomer liquid on an upper plaster model, taken of the patient to be fitted with the orthodontic appliance.

The mechanism portion (72) of the expansion assembly (12) that contains the adjustment mechanism (21) for screw (20) and the exposed elements of the orthodontic appliance, that are adjacent to the acrylic halves (16, 18) are coated and held in place with sticky wax, that may be removed with hot water or steam near the final stage of the manufacturing process. The polymer and monomer are then applied to the plaster model with the anchor elements of the appliance set in place, to be embedded securely in the acrylic palate of the orthodontic appliance. Once the acrylic is set and hardened, the acrylic palate is then manually cut, as desired, along its symmetric midline to form the aforementioned two acrylic halves (16, 18).

One "Hang Clasp" (58) (shown in FIGS. 5-8 as orthodontic clasps 56, 58) as used throughout this specification, are used with the Hang Expander orthodontic appliance, and may be used with many other orthodontic appliances. The Hang Clasp, orthodontic clasp (58) as shown in FIGS. 5-8, is a welded and soldered two piece metal clasp. The clasp comprises two substantially equal length wires (81, 82) best seen in FIG. 4, soldered together at a point (80) to form two substantially equal length long ends (83, 84) and two substantially equal length short ends (85, 86) best seen in FIGS. 1, 2 and 3. The short wires, as seen in FIG. 4, are bent into a shape (FIGS. 1-3) to create a clasp around a molar, or other tooth, as shown in FIGS. 5-8.

Method of Manufacturing the Orthodontic Clasp

The orthodontic clasp may be manufactured as disclosed below. Variations may be made in the manufacture of the orthodontic clasp, such as in the gauge or type of wire used, to accommodate patient's special needs or manufacturing efficiency. Such variant embodiments, and each of them, are intended to be covered by the present inventive concept and this patent. orthodontic appliances would typically use two orthodontic clasps, as shown in FIGS. 4 and 5, with one orthodontic clasp located on each side of the orthodontic appliance.

The orthodontic clasp may be manufactured using a 0.032 inch gauge, heat treated stainless steel wire, cut to two lengths, each length being approximately 3.5 inches long. The two lengths of wire are then spot welded together in place, about ¾ down the length, at a set of angles between approximately 20° and 160° to between approximately 60° and 120°, as per a patient's needs. Then, a silver solder flux is placed on the weld/solder joint (80), using a pin flame from a butane torch or the like. This combination weld and solder joint (80) further maintains the strength of weld/solder joint (80). When applying the silver solder to the weld, one should be careful not to overheat the wire and to let solder flow and cool and then set. Weld/solder joint (80) can also be made with laser welding or electrical welding according to accepted standards with those techniques. The four wires extending from weld/solder joint (80) are then bent at a rounded and non-sharp approximate right angle, so that the newly formed orthodontic clasp, in its rough form, would fit over the desired molar of a patient. These four wire bends (83', 84', 85', 86') are the clasp wire bends.

A set of holes are then drilled into the model made of the patient's palate and teeth, Said model may be composed of a plaster, polymeric, rubber, or plastic material, Two holes are drilled on each side of the model in the upper primary second molar area where the wire ends of two of the four wire segments extending from the weld/solder joint (80) will later be inserted on each side, said two wire ends being the mesial wire (86) and the distal wire (85).

A liquid separating medium, such as Liquid Foil Separator from Great Lakes Orthodontic Products, is then applied to the entire palate area of the upper model, to prevent acrylic (16, 18) 290 from sticking to the upper model. A 3-prong pliers, or the like, is then used to bend and cut two adjacent wires on the orthodontic clasps, the mesial wire (86) and the distal wire (85), that are at an approximately angle of between approximately 120° and 160°, and cut to a length to be inserted into the model's two holes, cited above, and made to fit between the two embrasures of the upper primary second molars, The ends of the mesial wire (86) and the distal wire (85) are then ground and sharpened to points at the terminal ends of the wires, using a power green stone grinder or the like, to more easily fit these wires into the two embrasures of the upper primary second molars, The mesial wire point and the distal wire point allow the mesial wire (86) and the distal wire (85) to more easily fit into the embrasures of the tooth.

The two opposite wires on the orthodontic clasp are the clasp anchors (83, 84), and each passes between the two embrasures of a tooth (60, 62) and are each bent behind the tooth (60, 62) with an anchor wire bend (83', 84') to where the end portions of the two clasp anchors (83, 84) are to be embedded in the acrylic (16, 18). The end portion of each of the two clasp anchors (83, 84) are bent, using a 3-prong pliers or the like, to form a plurality of crimps, or the like. These crimps further prevent the orthodontic clasp (56, 58) from rotating or moving when in use, embedded in the acrylic (16, 18) portion of an orthodontic appliance.

When manufacturing an orthodontic appliance, sticky wax is then applied on all the wires intended to be in contact with the teeth and not intended to be embedded in the acrylic (16, 18) portion of the orthodontic appliance. Once the orthodontic clasps and other elements of an orthodontic appliance have been embedded into the acrylic, prepared using a cold-cured or salt and pepper process, multiple times, where a special polymer powder is applied, followed by a special monomer fluid, which solidifies the acrylic, as desired, instant hot water may then be applied to melt and thereby remove the sticky wax from the orthodontic clasp, and the orthodontic appliance and the model. This step using sticky wax, in the manufacturing process, need not be made when solely manufacturing the orthodontic clasp, or for the manufacture of the orthodontic clasp for use in kits and the like, for later use in manufacturing an orthodontic appliance.

In short, a method of manufacturing the orthodontic clasp is comprised essentially of the following steps:

a. measuring and cutting two wires, each approximately 3.5 inches long;

b. welding and then soldering said two wires together at an angle, about % down the length, thereby forming a weld/solder joint;

c. bending the four wire segments extending from said weld/solder joint, gently to a rounded and non-sharp angle of approximately 90°, thereby forming four clasp wire bends;

d. cutting two of said four wire segments that are adjacent to each other, thereby forming a mesial wire and a distal wire, with said mesial wire and said distal wire cut to a length to comfortably fit into the embrasures of a molar or bicuspid tooth, when said orthodontic clasp is in use;

e. sharpening the end of the mesial wire to a mesial wire point and sharpening the end of the distal wire to a distal wire point;

f. cutting the two other adjacent wire segments of the four wire segments, thereby forming two anchor wires, to a length to properly anchor the orthodontic clasp when properly embedded into an acrylic portion of an orthodontic appliance, when said orthodontic clasp is in use;

g. bending said two anchor wires near their ends, so that each of the anchor wires has a plurality of small crimps; and h. bending each of the two anchor wires, with an anchor wire bend, so that said anchor wires may be properly embedded into an acrylic portion of an orthodontic appliance, when in use.

Kits for the Assembly of the Orthodontic Clasp

Kits for the manufacture and assembly of the orthodontic appliances may include the materials used in the Method of Manufacturing, disclosed above, or may include some pre-assembled elements of the invention, or some partially assembled elements of the invention, or a combination thereof. Such pre-assembled elements may include a rough pre-assembled or partially assembled orthodontic clasp, with one or more of the following elements included, such as a plurality of clasp wire bends, a weld/solder joint, a mesial wire, with or without a mesial wire point, a distal wire, with or without a distal wire point, and two clasp anchors, with anchor wire bends and crimps.

Alternatively, a kit may include one or more partially assembled orthodontic clasps with only the weld/solder joint completed, but without the more precise and patient specific work completed on each orthodontic clasp's four wire segments extending from the weld/solder joint, that is, the two anchor wires and the mesial wire and the distal wire.

While I have shown and described in this disclosure and its appended drawing figures, and which are a part of and incorporated in said disclosure, only selected embodiments in accordance with the present invention, it is understood that the same is not limited thereto, but is susceptible to numerous changes and modifications as known to one having ordinary skill in the art, and I therefore do not wish to be limited to the details shown and described herein, but instead to cover all such modifications, changes, eliminations, combinations and hybrids, as are encompassed by the scope of the appended claims, including, but not limited to kits, partial kits, or the like, for the manufacture of the orthodontic appliance, and further including pre-assembled or partially assembled kits for the manufacture of the orthodontic appliance.

I claim:

1. An orthodontic clasp, consisting of:
   two substantially equal length metal wires soldered together at only one single point, to form two substantially equal length long ends and two substantially equal length short ends, the two short ends bent into a shape to create a clasp around a tooth and the two long ends adapted to create clasp anchors.

2. The orthodontic clasp of claim 1, said solder point being about three quarters down the length of both wires at a set of angles between about 20° and 160° to between about 60° and 120°, said two longer wire segments each being a clasp anchor and said two shorter wire segments being a mesial wire and a distal wire.

3. The orthodontic clasp of claim 2, in which said mesial wire has a mesial wire point at the mesial wire's end and said distal wire has a distal wire point at the distal wire's end.

4. The orthodontic clasp of claim 1, in which said weld/solder the solder joint comprises solder composed essentially of silver.

5. The orthodontic clasp of claim 1, in which the two metal wires are composed essentially of stainless steel.

6. The orthodontic clasp of claim 1, in which each of said clasp anchors has an anchor wire bend located after said clasp wire bend.

7. The orthodontic clasp of claim 6, in which each of said clasp anchors has a plurality of crimps located after said anchor wire bend.

8. The orthodontic clasp of claim 1, in which said orthodontic clasp is adapted to be connected to an orthodontic appliance.

9. The orthodontic clasp of claim 8, in which said orthodontic appliance has an acrylic portion and said orthodontic clasp is adapted to be connected to said orthodontic appliance by a portion of said clasp anchors being embedded in said acrylic portion of said orthodontic appliance.

10. An orthodontic clasp, consisting of:
   a. two substantially equal length heat-treated stainless steel wires crossed at an angle and soldered together at only one single point, to form two substantially equal length long ends and two substantially equal length short ends, the two short ends bent into a shape adapted to create a clasp around a molar and the two long ends adapted to create clasp anchors;
   b. said solder point being about three quarters down the length of both wires at a set of angles between about 20° and 160° to between about 60° and 120° and having four wire segments extending from said two metal wires crossed at the solder point;
   c. said two equal length long ends being clasp anchors, having a plurality of crimps; and,
   d. said two equal length short ends being a mesial wire and a distal wire, said mesial wire having a mesial wire point at the mesial wire's end, and said distal wire having a distal wire point at the distal wire's end.

11. The orthodontic clasp of claim 10, in which said orthodontic clasp is adapted to be connected to an orthodontic appliance having an acrylic portion and each of said clasp anchors is adapted to be embedded in said acrylic portion of said orthodontic appliance.

12. The orthodontic clasp of claim 11, in which the orthodontic clasp wires are made of stainless steel having a wire gauge thickness of from about 0.030 inches to about 0.036 inches.

13. The orthodontic clasp of claim 12, in which the orthodontic clasp wires are made of stainless steel having a wire gauge thickness of about 0.032 inches.

\* \* \* \* \*

UNITED STATES PATENT AND TRADEMARK OFFICE
CERTIFICATE OF CORRECTION

PATENT NO. : 8,435,031 B2  
APPLICATION NO. : 12/783814  
DATED : May 7, 2013  
INVENTOR(S) : Hang Page 1 of 1

It is certified that error appears in the above-identified patent and that said Letters Patent is hereby corrected as shown below:

In the Claims:

Column 9, Line 26, Claim 4:

After "The orthodontic clasp of claim 1, in which"
Delete "said weld/solder".

Signed and Sealed this
Tenth Day of September, 2013

Teresa Stanek Rea
*Acting Director of the United States Patent and Trademark Office*